US007374777B2

(12) United States Patent
Li et al.

(10) Patent No.: US 7,374,777 B2
(45) **Date of Patent: *May 20, 2008**

(54) ORIENTED BIOPOLYMERIC MEMBRANE FOR MENINGEAL TISSUE REPAIR

(75) Inventors: Shu-Tung Li, Oakland, NJ (US); Debbie Yuen, Woodcliff Lake, NJ (US); Peggy Hansen, Cedar Grove, NJ (US)

(73) Assignee: Collagen Matrix, Inc., Franklin Lakes, NJ (US)

(*) Notice: Subject to any disclaimer, the term of this patent is extended or adjusted under 35 U.S.C. 154(b) by 471 days.

This patent is subject to a terminal disclaimer.

(21) Appl. No.: 10/610,465

(22) Filed: Jun. 30, 2003

(65) Prior Publication Data

US 2004/0001877 A1 Jan. 1, 2004

Related U.S. Application Data

(63) Continuation-in-part of application No. 10/132,630, filed on Apr. 25, 2002, now Pat. No. 6,599,524, which is a continuation of application No. 09/291,835, filed on Apr. 14, 1999, now Pat. No. 6,391,333.

(51) Int. Cl.
*A61F 13/00* (2006.01)
*A61K 9/70* (2006.01)
*A61L 15/00* (2006.01)
*A01N 25/34* (2006.01)

(52) U.S. Cl. ...................... 424/443; 424/445; 424/447; 424/449; 424/402

(58) Field of Classification Search ................ 424/443, 424/402, 445, 447, 449

See application file for complete search history.

(56) References Cited

U.S. PATENT DOCUMENTS 3,157,524 A 11/1964 Artandi
4,418,691 A * 12/1983 Yannas et al. .............. 424/548
4,657,548 A 4/1987 Nichols
4,725,671 A 2/1988 Chu et al.
4,963,146 A 10/1990 Li
5,206,028 A 4/1993 Li
5,326,350 A 7/1994 Li
5,376,376 A * 12/1994 Li .............................. 424/443
5,512,291 A 4/1996 Li
6,391,333 B1 5/2002 Li et al.
6,599,524 B2 * 7/2003 Li et al. ..................... 424/443

OTHER PUBLICATIONS

Li et al. "Collagen as a Biomaterial: An application in Knee Meniscal Fibrocartilage Regeneration", Mat. Res. Soc. Symp. Proc. 331:25-32, 1994.

(Continued)

*Primary Examiner*—Isis Ghali
(74) *Attorney, Agent, or Firm*—Occhiuti Rohlicek & Tsao LLP

(57) ABSTRACT

A cell occlusion sheet membrane adapted for repairing a damaged meningeal tissue. The sheet membrane contains a layer of cross-linked, oriented biopolymeric fibers that has a thickness of 0.1 mm to 3.0 mm, a density of 0.1 g/cm$^3$ to 1.2 g/cm$^3$, a hydrothermal shrinkage temperature of 45° C. to 80° C., a suture pullout strength of 0.1 kg to 5 kg, a tensile strength of 10 kg/cm$^2$ to 150 kg/cm$^2$, and permeability to molecules having molecular weights of 200 to 300,000 daltons. Also disclosed is a method for making the membrane.

20 Claims, 1 Drawing Sheet

OTHER PUBLICATIONS

Li "Biologic Biomaterials: Tissue-Derived Biomaterials (Collagen)", The Biomedical Engineering Handbook, pp. 627-647, 1995.

Oneson et al. "The Preparation of Highly Purified Insoluable Collagens", The Journal of the American Leather Chemist Associate 9:440-450, 1979.

* cited by examiner

ORIENTED BIOPOLYMERIC MEMBRANE FOR MENINGEAL TISSUE REPAIR

RELATED APPLICATIONS

This application is a continuation-in-part of and claims priority to U.S. application Ser. No. 10/132,630, filed Apr. 25, 2002, now U.S. Pat. No. 6,599,524, which is a continuation of U.S. application Ser. No. 09/291,835, filed Apr. 14, 1999, now U.S. Pat. No. 6,391,333, the contents of which are incorporated herein by reference.

BACKGROUND OF THE INVENTION

Medical applications of biopolymeric membranes are manifold. See, e.g., Shu-Tung Li, Biologic Biomaterials: Tissue-Derived Biomaterials (Collagen). In: Biomedical Engineering Handbook, Ed. J. D. Bronzino, 627-647, CRC Press, Inc. Boca Raton, Fla., 2000.

Biopolymeric membranes, such as collagen membranes, can be made by air-drying a biopolymeric fibers-containing solution, or applying an acid or a base solution of dispersed biopolymeric fibers on a flat surface. Li disclosed in U.S. Pat. No. 5,206,028 a method of preparing a collagen membrane by first freeze-drying a collagen dispersion to form a sponge, which is then humidified, compressed, and subjected to chemical crosslinking. Chu et al., on the other hand, disclosed in U.S. Pat. No. 4,725,671 a method of preparing a gel from an atelocollagen solution and then compressing and air-drying the gel to form a collagen membrane.

The biopolymeric fibers in sheet membranes prepared by the prior art methods are randomly oriented. Such membranes generally have low mechanical strength and are only useful in applications where mechanical strength of the device is not a critical factor for function. They are not suturable and tend to tear with a slight suture tug. As most soft tissue enforcement materials require extensive mechanical strength so that they can be easily secured in place either by using sutures, staples, tags, or screws, mechanical strength becomes a critical factor in designing biopolymeric fiber-based membranes for applications in soft tissue repair.

SUMMARY OF THE INVENTION

An aspect of this invention relates to a cell occlusion sheet membrane containing at least one layer of cross-linked, oriented biopolymeric fibers, such as collagen fibers. What is meant by “oriented” is that at least half of the biopolymeric fibers are in one general direction (i.e., “fiber orientation”) as determined by the method described below or by an analogous method. What is meant by “cell occlusion” is that a membrane will not allow cells to migrate across the membrane during the initial period of healing in vivo in guided tissue repair and regeneration process. The sheet membrane is generally flat but, if desired, can be somewhat curved. It has a thickness of 0.1 mm to 3.0 mm (preferably, 0.2 mm to 1.0 mm), a density of 0.1 g/cm$^3$ to 1.2 g/cm$^3$ (preferably, 0.2 g/cm$^3$ to 0.8 g/cm$^3$), a hydrothernal shrinkage temperature of 45° C. to 85° C. (preferably, 50° C. to 70° C.), a suture pullout strength (both perpendicular and parallel to the fiber orientation) of 0.1 kg to 5 kg (preferably, 0.3 kg to 3 kg), and a tensile strength of 10 kg/cm$^2$ to 150 kg/cm$^2$ (preferably, 30 kg/cm$^2$ to 80 kg/cm$^2$), and is permeable to molecules having molecular weights of 200 to 300,000 daltons (preferably, 1,000 to 50,000 daltons). The above recited parameters can be readily measured by methods known to a person of ordinary skill in the art, some of which are described in detail below.

When a sheet membrane is made of two or more layers of oriented biopolymeric fibers, the layers are secured to each other by fibrin glue, collagen glue (gel or moist collagen sponge), suture (resorbable or nonresorbable), crosslinking formation, or the like. Preferably, the biopolymeric fibers in different layers are respectively oriented in different directions.

Another aspect of this invention relates to a method of making a single-layer sheet membrane of oriented biopolymeric fibers. The method includes: (1) reconstituting biopolymeric fibers, e.g., collagen fibers, dispersed in a solution; (2) placing the reconstituted biopolymeric fibers around a mandrel; (3) rotating the mandrel to convert the reconstituted biopolymeric fibers on the mandrel into a tubular membrane of oriented biopolymeric fibers; (4) cutting the tubular membrane longitudinally after it has been dried on the mandrel; (5) rolling the cut membrane into a tubular form that is an inversion of the tubular membrane; (6) inserting the rolled membrane into a tubular mesh; and (7) crosslinking the biopolymeric fibers to form a sheet membrane of oriented biopolymeric fibers.

Another aspect of this invention relates to the use of repairing meningeal tissue using the oriented sheet biopolymeric membranes for fixing the membrane with the host tissues using sutures or the like.

DETAILED DESCRIPTION OF THE INVENTION

Figure 1:
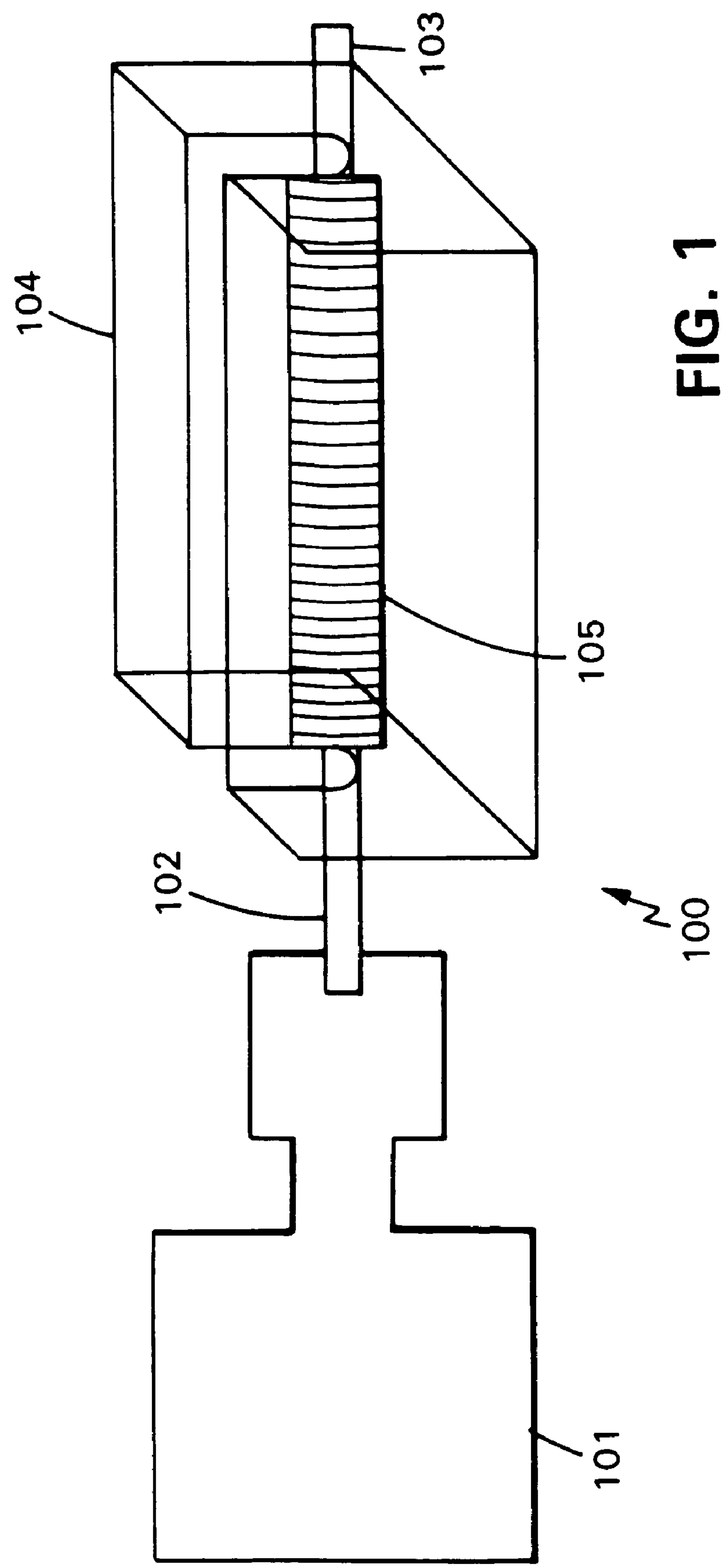
FIG. 1 is a fabrication apparatus for orienting reconstituted biopolymeric fibers.

The membranes of the present invention for meningeal tissue repair contain at least one layer of biopolymeric fibers oriented in one direction, and therefore possess greater mechanical strength and tear resistance. The improved properties allow such membranes to be sutured into place at the meningeal repair site.

Such membranes can be produced by dispersing biopolymeric fibers in an aqueous solution; reconstituting the dispersed fibers in one layer; and orienting the reconstituted fibers. The membranes may include selected bioactive agents such as growth factors, anti-adhesive molecules, drugs, and the like.

Below are examples of how different membranes of this invention can be prepared.

A method of fabricating a reconstituted single-layer membrane of the present invention includes the following steps:

a) forming an aqueous dispersion containing biopolymeric fibers;
b) reconstituting the fibers;
c) orienting the reconstituted fibers on a rotating mandrel to form a tubular membrane;
d) compressing the hydrated fibers to remove excess solution;
e) drying the oriented fibers on the mandrel;
f) cutting the membrane perpendicular to the orientation of the fibers;
g) inverting the membrane; and
h) crosslinking the membrane.

A method of fabricating a reconstituted two-layer membrane of the present invention includes the following steps:

a) dispersing fibers in an aqueous solution;
b) reconstituting the dispersed fibers;
c) orienting the reconstituted fibers on a rotating mandrel to form a tubular membrane;
d) compressing the hydrated fibers to remove excess solution;
e) drying the compressed fibers;
f) cutting the membrane perpendicular to the orientation of the fibers to form a sheet membrane;
g) placing around the sheet membrane a second sheet membrane prepared in the same manner;
h) inverting the two-layer membrane;
i) crosslinking the membrane; and
j) stabilizing the two layers of membrane.

A method of fabricating a reconstituted three-layer membrane of the present invention includes the following steps:

a) dispersing fibers in an aqueous solution;
b) reconstituting the dispersed fibers;
c) orienting the reconstituted fibers on a rotating mandrel to form a tubular membrane;
d) compressing the hydrated fibers to remove excess solution;
e) overlaying a prefabricated membrane around the tubular membrane on the mandrel;
f) orienting the reconstituted fibers again around the prefabricated membrane on the rotating mandrel;
g) compressing the hydrated fibers to remove excess solution;
h) drying the compressed fibers on the mandrel;
i) cutting the dried three-layer tubular membrane perpendicular to the orientation of the fibers to form a three-layer sheet membrane;
j) inverting the membrane; and
k) crosslinking the membrane.

Type I collagen fibers are preferred for preparing the membranes of the present invention due to its biocompatibility and easy accessibility. Other biopolyrneric materials, which can be either natural or synthetic, include but are not limited to, other types of collagen (e.g., type II to type XXI), elastin, fibrin, polysaccharide (e.g., chitosan, alginic acid, cellulose, and glycosaminoglycan), a synthetic analog of a biopolymer by genetic engineering techniques, or a combination thereof.

Depending on the particular clinical application, orientation of the fibers in a membrane can be of particular importance. For example, in many surgical applications, a patch material is needed to enforce a diseased tissue. Thus, in repair of a dura mater, an oriented membrane will provide a much higher strength than a random oriented membrane such as the currently marketed dura repair device (DuraGen, Integra LifeSciences), such that the oriented membrane can be sutured with the host dura membrane to prevent the cerebral spinal fluid leakage.

Controlling the fiber orientation in a reconstituted membrane optimizes the desired function of the membrane in vivo. Generally, the suture pullout strength is higher in the direction perpendicular to the fiber orientation than in the direction parallel to the fiber orientation, whereas the tensile strength is stronger in the oriented fiber direction than the direction perpendicular to the fiber orientation. A membrane made of two or more layers of oriented biopolymeric fibers affords an enhanced suture pullout strength and mechanical strength in the respective directions.

In particular, a collagen-based membrane of the present invention may be prepared by the following methods.

First, a native source of type I collagen, such as skin, bone, tendon, or ligament is cleaned, washed, and non collagenous impurities removed by methods well known in the art such as that disclosed in U.S. Pat. No. 5,512,291 and in Oneson, et al., J. Am. Leather Chemists Assoc. 65:440-450, 1970.

Next, a collagen dispersion is prepared. Generally, the purified collagen material is dispersed in an acid solution. Either an organic acid such as acidic ($CH_3COOH$) or lactic acid $CH_3CHOHCOOH$) or an inorganic acid such as hydrochloric acid (HCl) or sulfuric acid ($H_2SO_2$) may be used. The preparation of a collagen fiber dispersion is well known in the art such as those disclosed in U.S. Pat. Nos. 3,157,524 and 5,326,350. These patents are included as references as if set out in full. The solid content of collagen fibers in the dispersion suitable for the present invention is generally between 0.5% to 1.5%. Alternatively, a collagen dispersion may be prepared in an alkaline solution. Sodium hydroxide (NaOH), potassium hydroxide (KOH), calcium hydroxide ($Ca(OH)_2$) are the common bases that may be used to prepare the alkaline dispersed collagen. If it is desirable to include a bioactive molecule such as growth factors and antibodies or the like into the membrane, the bioactive molecule may be dissolved and mixed with the dispersed collagen in the dispersion.

An aliquot of acid dispersed collagen fibers is weighed into a flask. The dispersed collagen is reconstituted by neutralizing the acid with a base (such as $NH_4OH$ or NaOH) to a pH of about 5, the isoelectric point of this purified material. Other reconstituting agents such as neutral salts, non-aqueous solvents or the like may be used to reconstitute the collagen fibers. The reconstituted, but still highly hydrated, collagen fibers are oriented by winding the fibers onto a rotating mandrel. Shown in FIG. 1 is an apparatus that is used for winding the reconstituted collagen fibers. The apparatus 100 comprises a motor 101, an adapter 102, a mandrel 103 fit into an adapter 102, and a dispersion housing chamber 104. The reconstituted collagen fibers are first slowly poured into the chamber 104. The motor 101 with a predetermined speed is then turned on, causing the reconstituted fibers 105 to be wound onto the mandrel 103 to form a tubular membrane.

The excess solution associated with the tubular membrane can be removed by compressing the rotating mandrel against a smooth surface such as a glass or a plastic sheet. The partially dehydrated, oriented membrane is then dried. Depending on the desired permeability properties of the membrane, the drying can either be by air- or freeze-drying. Air-drying produces a membrane which allows the permeation of ions or small peptides (with molecular weight less than 2,000), whereas the freeze-dried membranes permit the permeation of molecules ranging from molecular weight from 200 to 300,000 (such as various growth factors and bioactive macromolecules). Desired permeability properties of the membranes can be obtained by controlling the extent of dehydration prior to freeze-drying.

The dried tubular membrane is then removed from the mandrel and cut along the long axis of the tube. The cut membrane is then inverted to a tubular form so that the inner (outer) wall of the original tube becomes the inner (outer) wall. If necessary, the curvature of the inverted tube can be adjusted by creating an overlap between the two cutting edges or by leaving a gap between them. The inverted tube, having a reversed curvature, is inserted into a tubular mesh and crosslinked with a crosslinking agent such as an aldehyde compound. Crosslinking of the inverted membrane under a certain reversed curvature forces the membrane into a flat sheet geometry after crosslinking. Preferably, the tubular mesh is adjustable diameter so that it can accommodate inverted membranes of all curvatures. Depending on the thickness of the membrane, a larger or smaller diameter tubular mesh may be used. The tubular mesh may be constructed from biocompatible metals or plastics (e.g. stainless steel and polypropylene).

The speed of rotation of the mandrel affects the degree of orientation of the collagen fibers in a given direction. Generally, a high speed of rotation of the mandrel (e.g., >700 rpm) generates a higher degree of fiber orientation than a low speed rotation (e.g., <50 rpm). Depending on the overall mechanical property requirements, the degree of orientation can be adjusted by the speed of rotation of the mandrel.

The degree of fiber orientation also depends on the diameter of the mandrel. All else being the same, a mandrel with a smaller diameter produces a higher degree of fiber orientation. Preferably, the mandrel has a diameter of about 1.0 cm to about 3.0 cm. However, other sizes may also be used if desired.

Another factor that contributes to the fiber orientation is the amount of reconstituted fibers per unit volume. The amount of collagen fibers per unit volume defines the thickness of the membrane of a given diameter of the mandrel. Preferably, the amount of collagen fibers (dry weight) per cm length of a 1.25 cm-diameter mandrel is in the range of about 0.2 grams to about 0.8 grams. The thickness of the dry membrane produced is in the range of about 0.2 mm to about 0.8 mm.

The degree of orientation can be determined by measuring and comparing the acute angles of intersection between the fibers and a fixed axis, e.g., the long axis of the tubular membrane. In order to facilitate the determination of the angles of intersection, a dye such as methylene blue may be used to stain the fibers and the acute angles of intersection of various fibers with respect to the fixed axis can then be easily measured with a protractor.

The extent of crosslinking determines the in vivo stability of the membrane. Depending on the functional requirements in vivo, the extent of crosslinking may be controlled accordingly. The extent of crosslinking in solution phase may be controlled by concentration, temperature, pH, and time of crosslinking. The crosslinking in vapor may be controlled by vapor pressure, temperature, and time of crosslinking.

For membranes used to repair the dura mater tissue it is desirable that the membranes be stable in vivo for about 16 to 36 weeks.

In vivo stability depends on the nature of the crosslinks formed by various crosslinking agents. Generally, glutaraldehyde forms more stable crosslinks than formaldehyde and carbodiimide. Thus, glutaraldehyde has been used to crosslink tissue heart valves for in vivo durability, and formaldehyde has often been used to crosslink resorbable implants.

The extent of crosslinking may be determined by methods well known in the art such as by monitoring the hydrothermal shrinkage temperature or by determining the number of intermolecular crosslinks. In general, a hydrothermal shrinkage temperature in the range of 50° C. to 55° C. results in vivo stability for 8-16 weeks, and the hydrothermal shrinkage temperature in the range of 45° C. to 60° C. results in in vivo stability for 12 to 36 weeks. For in vivo stability greater than 6 months, the shrinkage temperature should be tailored in the range of 55° C. to 75° C.

If it is desirable to have a specifically designed surface active membrane, then chemical modification methods may be used to covalently link a bioactive molecule on the surface of the membrane. The surface functional groups of collagen such as the side-chain amino groups of lysines and hydroxylysines, the side-chain carboxyl groups of aspartic and glutamic acids, and the side-chain hydroxyl groups of hydroxyproline and serines and threonines can be coupled with reactive functional groups of the bioactive molecules to form covalent bonds using coupling agents well known in the art such as aldehyde compounds, carbodiimides, and the like. Additionally, a spacer molecule may be used to gap the surface reactive groups in collagen and the reactive groups of the bioactive molecules to allow more flexibility of such molecules on the surface of the membrane.

In a two-layer membrane, the fiber orientations can be designed so as to enforce the mechanical properties in two directions. Specifically, a two-layer membrane is formed by overlaying a prefabricated layer on the top of another. By controlling the angle of fiber orientations between the two layers, mechanical properties of the bilayer membrane are defined. The two layers can be secured to each other by a biological glue such as collagen glue, fibrin glue, or the like, or by sutures. The two layers can be further secured to each other by crosslinking formation using crosslinking agents such as aldehyde compounds. The process can be repeated to produce as many layers as needed, such that the final fiber orientation geometry and the mechanical properties are strictly correlated and controlled.

Alternatively, a multi-layer membrane can be constructed directly on the rotating mandrel. Using reconstituted fibers, a single-layer membrane is first cast on a rotating mandrel. A prefabricated single-layer membrane sheet is then wrapped around the first membrane in such a way so that the fiber orientations of the two membranes intersect at a desirable angle. A second membrane is then cast on the top of the overlaid prefabricated membrane, forming a sandwich-like structure with controlled fiber orientations. If necessary, additional layers may be added in an analogous manner. The process can be manipulated to produce a variety of constructs with predetermined fiber orientations and mechanical properties. The multi-layer membranes can be secured by chemical crosslinking.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Preparation of Purified Collagen Fibers

The fat and fascia of bovine flexor tendon were carefully removed and washed with water. The cleaned tendon was frozen and comminuted by slicing into 0.5 mm slices with a meat slicer. 1 kg of sliced wet tendon was first extracted in 5 liters of distilled water at room temperature for 24 hours. The extractant was discarded and the 5 liters of 0.2 N HCl in 0.5 M $Na_2SO_4$ was added and the tendon slices were extracted at room temperature for 24 hours. The acid solution was discarded and 5 liters of 0.5 M $Na_2SO_4$ was added to wash the tendon and to remove the residual acid. The acid extracted tendon was then extracted in 5 liters of 0.75 M NaOH in the presence of 1 M $Na_2SO_4$ at room temperature for 24 hours. The base solution was then discarded. The residual base was neutralized with 0.01 N HCl to pH 5 followed by several changes of distilled water to remove the residual salts associated with the purified tendon. The tendon was then defatted with isopropanol (tendon: isopropanol=1:5, v/v) for 8 hours at 25° C. under constant agitation. The extractant is decanted and an equal volume of isopropanol was added and the tendon slices were extracted overnight at 25° C. under constant agitation. The defatted tendon was then dried under a clean hood. The purified collagen fibers were stored dry at room temperature for further processing.

Preparation of Collagen Fiber Dispersions

A. Preparation of Acid Dispersed Collagen Fibers

Purified collagen fibers were weighed and dispersed in 0.07 M lactic acid, homogenized with a Silverson Homogenizer (East Longmeadow, Mass.), and then filtered with a stainless steel mesh filter (40 mesh). The dispersion, which had a collagen content of 0.7% (w/v), was deaerated with vacuum to remove the trapped air.

B. Preparation of Alkaline Dispersed Collagen Fibers

Alternatively, purified collagen fibers were weighed and dispersed in 0.005 M NaOH, homogenized with a Silverson Homogenizer (East Longmeadow, Mass.), and then filtered with a stainless steel mesh filter (40 mesh). The dispersion, which had a collagen content of 1.0% (w/v), was deaerated with vacuum to remove the air trapped in it.

Fabrication of a Single-layer Oriented Membranes

Acid dispersed collagen fibers (180 g) were reconstituted by adding 20 ml of 0.3% $NH_4OH$ to its isoelectric point (pH 4.5-5.0). The reconstituted fibers were poured into a fabrication apparatus with a mandrel of 2.54 cm in diameter and were evenly distributed manually (FIG. 1). The fibers were oriented by rotating the mandrel at 250 rpm to form a tubular membrane. The excess solution was removed from the tubular membrane on the mandrel by compressing the membrane against two glass plates. The partially dehydrated fibers on the mandrel were freeze-dried (−10° C. for 24 hours, 20° C. for 16 hours at a pressure less than 200 millitorr) using a Virtis Freeze Dryer (Gardiner, N.Y.). The dried tubular membrane of fibers was cut along the longitudinal direction, i.e., perpendicular to the fiber orientation. The cut membrane was physically fixed in a sandwich form between two semi-tubular stainless steel screens with the curvature of the membrane reversed, and crosslinked with formaldehyde vapor generated from a 2% HCHO solution at 22° C. for 5 to 10 hours. The crosslinked membranes were extensively rinsed in distilled water and freeze-dried.

Fabrication of a Two-layer Oriented Membrane

A collagen glue was first prepared as follows: Alkaline dispersed collagen fibers were freeze-dried under standard freeze drying conditions (−10° C. for 48 hours, 20° C. for 16 hours at a pressure less than 200 millitorr) using a Virtis Freeze Dryer to form a sponge. The freeze-dried sponge was cut to the same size as the size of a single-layer oriented membrane which had not been subjected to crosslinking. The sponge was humidified for 8 hours at 25° C. with water vapor in a closed container. The humidified sponge was sandwiched between two uncrosslinked single-layer oriented membranes in such a way that the orientation of one membrane was about 90° respect to that of the other membrane. The whole composite was compressed using a mechanical press to form a cohesive membrane composite. The membrane was then crosslinked with HCHO vapor similar to that described above.

Alternatively, one crosslinked oriented membrane was overlaid over another with the fiber orientations of the two membranes intersecting at an angle of about 90 degrees. The two overlaid membranes were sutured together using a 3-0 Dexon suture (Davis and Geck, Danbury, Conn.).

Fabrication of Three-layer Oriented Membrane

Two humidified collagen sponges prepared in a manner described above were sandwiched between three uncrosslinked oriented collagen membranes with the fiber orientations of the two top membranes intersecting at an angle of about 60 degrees and those of the two bottom membranes also at the same angle. The composite membrane was then crosslinked in a manner described above.

Alternatively, three crosslinked oriented membranes were sutured together with a 3-0 Dexon suture.

Mechanical Characteristics of Oriented Membranes

A. Fiber Orientation

The fiber orientation of an oriented membrane of this invention is determined by first staining the fibers with a dye material (such as methylene blue for collagen fibers). The acute angle of intersection between a reference line (e.g., a line corresponding to the long axis of the mandrel used to prepare the membrane) and a fiber can then be readily measured. Such angles are measured for a statistically significant number of fibers. In each layer of an oriented membrane of this invention, the acute angles for at least 50" 10% of the fibers, with respect to the reference line, are within a relatively narrow range, i.e., "30 degrees.

B. Thickness

The thickness of the membrane is determined with a caliper. The thickness of a membrane of the present invention is generally within 0.1 mm to 3.0 mm.

C. Density

To determine the density (g/cm$^3$) of a membrane, the membrane is first dried under vacuum for 24 hours or over $P_2O_5$ for 24 hours and the dry weight is recorded. The dimensions (length, width and thickness) of the membrane are then measured with a caliper. Thus, the density is a measure of the amount of per unit volume of the membrane. The density of a membrane of the present invention is in the range of 0.1 g/cm$^3$ to 1.2 g/cm$^3$.

D. Hydrothermal Shrinkage Temperature

A membrane having the dimensions 1.5 cm×2.0 cm is attached to a shrinkage temperature apparatus. See Li et al., Mat. Res. Soc. Symp. Proc. 331:25-32, 1994. The sample is first equilibrated in a beaker of phosphate buffer saline (PBS). The solution is heated at a rate of 1° C. per minute. The length of the samples is continuously recorded. The hydrothermal shrinkage temperature of the membrane is defined as the temperature at which the length starts to change (onset point). The shrinkage temperature of a membrane of this invention is in the range from 50° C. to 85° C.

E. Mechanical Strength

Suture Pullout Strength Perpendicular to Fiber Orientation:

The suture pullout strength of the wet membrane with suture pulling direction perpendicular to the fibers is determined with a mechanical tester (Chatillon, Greensboro, N.C.). The membrane is cut along the direction perpendicular to the fiber orientation to a size of 20 mm×15 mm and soaked in phosphate buffered saline, pH 7.4 at 25° C., for about 2 minutes. A suture (3-0 silk black braided, taper SH-1, Ethicon, Somerville, N.J.) is placed through the 20 mm membrane side at approximately 4 mm from the edge. The suture is tied into a knot and is secured to the hook adapter of the tensile tester. The sample is then clamped. The sample is pulled at a speed 1.0 in/min until the suture is pulled out. The suture pull out strength of a membrane of this invention is in the range from 0.1 kg to 5.0 kg.

Suture Pullout Strength Parallel to Fiber Orientation:

The suture pullout strength of the membrane having fibers parallel to the suture pulling direction is determined with a mechanical tester (Chatillon, Greensboro, N.C.). The membrane is cut along the direction parallel to the fiber orientation to a size of 20 mm×15 mm and soaked in phosphate buffered saline, pH 7.4 at 25° C., for about 2 minutes the test is performed as described above. The suture pull out strength of a membrane of this invention is in the range from 0.1 kg to 5.0 kg.

Tensile Strength Perpendicular to the Fiber Axis:

The mechanical strength of the wet membrane being pulled in the direction perpendicular to the fibers is determined with a mechanical tester (Chatillon, Greensboro, N.C.). The membrane is cut along the direction perpendicular to the fiber orientation into a dumbbell shape with a die punch. The sample is soaked in phosphate buffered saline, pH 7.4, at 25° C. for about 2 minutes. The sample is then secured to a clamp fixture, and pulled at a speed 1.0 in/min until the sample is pulled apart. The tensile strength of a membrane of this invention is in the range from 10 kg/cm$^2$ to 150 kg/cm$^2$.

Tensile Strength Parallel to the Fibre Axis:

The mechanical strength of the wet membrane being pulled in the direction parallel to the fibers is determined with a mechanical tester (Chatillon, Greensboro, N.C.). The membrane is cut along the direction parallel to the fibre orientation into a dumbbell shape with a die punch. The sample is soaked in phosphate buffered saline, pH 7.4 at 25° C., for about 2 minutes. The test is performed as described above. The tensile strength of a membrane of this invention is in the range from 10 kg/cm$^2$ to 150 kg/cm$^2$.

F. Permeability

A 2-cm diameter disk cut from a membrane of this invention is inserted into a hole between two compartments of a specially designed chamber, thereby completely separating the two compartments. A fixed volume of PBS containing 50 μg of various sizes of peptide and protein molecules per ml is added to one compartment. The other compartment is filled with a fixed volume of PBS only. The solutions in both compartments are allowed to equilibrate for 24 hours. An assay is then conducted to determine the sizes of the peptide and protein molecules in the compartment which initially only contained PBS. The membrane of this invention is permeable to molecules having molecular weights ranging from 200 to 300,000 daltons.

G. Cell Occlusion

2×10$^6$3T3 fibroblasts are cultured in 200 μl medium on the top center of each membrane that is cut to a 1 cm circle to fit (dry) in Millicell inserts in a 24-well cell culture plate. Each Millicell is prewet according to manufacture's instructions and each collagen matrix is incubated in medium for 24 hour (in the insert) prior to cell seeding.

Harvest is conducted at 24 hour and 72 hour. The membranes in the Millicell are cut circumferentially. After formalin fixation, each membrane is cut through the center and both cut sides embedded with the cut side up in paraffin. Step sections are made through each membrane and stained with H&E to show cells. Slides are examined and results photographed digitally. The membrane of this invention shows cells adhering on the surface with no infiltration of cells into the interstitial space.

Use of Oriented Membranes in Neural Surgery for Dura Repair and Regeneration

Adult New Zealand white rabbits (3-4 kg) were used for the study. The rabbits were anesthetized using xylazine (5 mg/kg) and ketamine (35 mg/kg) injected intramuscularly. The rabbits were maintained sedated using halothane (0.5-2%) via endotracheal tube. The scalp was cleaned and closely shaved and the skin was washed with a mixture of alcohol and betadine. The scalp was incised coronally and the skin was retracted and the periosteum opened and stripped from the calvarium using a periosteal elevator. Two (2) medial and 2 lateral 2.1 mm burr holes were placed to avoid the sagittal and transverse venous sinuses and orbital cavity. Bone wax and electrocautery was used to control bleeding. A Dremel motor tool was used to cut a trapezoid-shaped craniotomy and elevate the bone flap hinged on pericranium and muscle. The bone flaps were removed with care to avoid damage to the underlying meninges and cerebral cortex. Using a dural hook, the dura mater was gently lifted and incised. Angled irridectomy scissors was used to create an 8 mm×8 mm defect in the dura mater. A 1 cm$^2$ dura substitute, that has been soaked in sterile saline for 5 mins, was placed over the dura defect (1 mm overlap on dura) and sutured in place with 8-0 polyamide sutures (Ethicon). The bone flaps were replaced and the periosteum was closed with 3-0 chromic gut while the skin was closed with 2-0 vicryl suture.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A cell occlusion sheet membrane adapted for the repair of a damaged meningeal tissue comprising a layer of cross-linked, oriented biopolymeric fibers, wherein the membrane has a thickness of 0.1 mm to 3.0 mm, a density of 0.1 g/cm3 to 1.2 g/cm3, a hydrothermal shrinkage temperature of 45° C. to 80° C., a suture pullout strength of 0.1 kg to 5 kg, and a tensile strength of 10 kg/cm2 to 150 kg/cm2, and is permeable to molecules having molecular weights of 200 to 300,000 daltons, wherein the membrane is obtained by cutting a tubular membrane longitudinally and perpendicular to the fiber orientation.

2. The sheet membrane of claim 1 further comprising a second layer of oriented biopolymeric fibers secured to the first layer of oriented biopolymeric fibers, wherein the biopolymeric fibers of the first and second layers are respectively oriented in different directions.

3. The sheet membrane of claim 2 further comprising a third layer of oriented biopolymeric fibers secured to the second layer of oriented biopolymeric fibers, wherein the biopolymeric fibers of the first, second, and third layers are respectively oriented in different directions.

4. The sheet membrane of claim 1, wherein the biopolymeric fibers are collagen fibers.

5. The sheet membrane of claim 4 further comprising a second layer of oriented collagen fibers secured to the first layer of oriented collagen fibers, wherein the collagen fibers of the first and second layers are respectively oriented in different directions.

6. The sheet membrane of claim 5 further comprising a third layer of oriented collagen fibers secured to the second layer of oriented collagen fibers, wherein the collagen fibers of the first, second, and third layers are respectively oriented in different directions.

7. The sheet membrane of claim 1, wherein the membrane has a thickness of 0.2 mm to 1.0 mm, a density of 0.2 g/cm3 to 0.8 g/cm3, a hydrothermal shrinkage temperature of 50° C. to 70° C., a suture pullout strength of 0.3 kg to 3 kg, and a tensile strength of 30 kg/cm2 to 80 kg/cm2, and is permeable to molecules having molecular weight cutoff of 70,000 daltons.

8. The sheet membrane of claim 7 further comprising a second layer of oriented biopolymeric fibers secured to the first layer of oriented biopolymeric fibers, wherein the biopolymeric fibers of the first and second layers are respectively oriented in different directions.

9. The sheet membrane of claim 8 further comprising a third layer of oriented biopolymeric fibers secured to the second layer of oriented biopolymeric fibers, wherein the biopolymeric fibers of the first, second, and third layers are respectively oriented in different directions.

10. The sheet membrane of claim 4, wherein the membrane has a thickness of 0.2 mm to 1.0 mm, a density of 0.2 g/cm3 to 0.8 g/cm3, a hydrothermal shrinkage temperature of 50° C. to 70° C., a suture pullout strength of 0.3 kg to 3 kg, and a tensile strength of 30 kg/cm2 to 80 kg/cm2, and permeable to molecules having molecular weight cutoff of 70,000 daltons.

11. The sheet membrane of claim 10 further comprising a second layer of oriented collagen fibers secured to the first layer of oriented collagen fibers, wherein the collagen fibers of the first and second layers are respectively oriented in different directions.

12. The sheet membrane of claim 11 further comprising a third layer of oriented collagen fibers secured to the second layer of oriented collagen fibers, wherein the collagen fibers of the first, second, and third layers are respectively oriented in different directions.

13. The sheet membrane of claim 1 further comprising a bioactive agent.

14. The sheet membrane of claim 4 further comprising a bioactive agent.

15. The sheet membrane of claim 7 further comprising a bioactive agent.

16. The sheet membrane of claim 10 further comprising a bioactive agent.

17. A method of making a cell occlusion single-layer sheet membrane of oriented biopolymeric fibers, said method comprising:

reconstituting biopolymeric fibers dispersed in a solution;

placing the reconstituted biopolymeric fibers around a mandrel;

rotating the mandrel to convert the reconstituted biopolymeric fibers on the mandrel into a tubular membrane of oriented biopolymeric fibers;

cutting the tubular membrane longitudinally and perpendicular to the fiber orientation;

rolling the cut membrane into a tubular form that is an inversion of the tubular membrane;

inserting the rolled membrane into a tubular mesh; and crosslinking the biopolymeric fibers, thereby forming a sheet membrane of oriented biopolymeric fibers.

18. The method of claim 17, wherein the biopolymeric fibers are collagen fibers.

19. The sheet membrane prepared by the method of claim 17.

20. The sheet membrane prepared by the method of claim 18.

* * * * *